United States Patent [19]
Rizk et al.

[11] Patent Number: 5,411,613
[45] Date of Patent: May 2, 1995

[54] METHOD OF MAKING HEAT TREATED STAINLESS STEEL NEEDLES

[75] Inventors: Said Rizk, Monroe; William O. Powers, North Haven; W. Scott Samsel, Bristol, all of Conn.

[73] Assignee: United States Surgical Corporation, Norwalk, Conn.

[21] Appl. No.: 132,008

[22] Filed: Oct. 5, 1993

[51] Int. Cl.$^6$ ............................ C21D 6/02; C21D 9/26
[52] U.S. Cl. .................................. 148/606; 606/222; 163/5
[58] Field of Search ............... 148/606, 325, 326, 327; 606/222; 163/5

[56] References Cited

U.S. PATENT DOCUMENTS

| | | |
|---|---|---|
| 3,038,475 | 6/1962 | Orcutt . |
| 3,408,178 | 10/1968 | Myers et al. . |
| 4,180,420 | 12/1979 | Sastri et al. . |
| 4,203,782 | 5/1980 | Yamada . |
| 4,326,885 | 4/1982 | Larson et al. . |
| 4,378,246 | 3/1983 | Hoshino et al. . |
| 4,453,987 | 6/1984 | Arai et al. . |
| 4,602,636 | 7/1986 | Noiles . |
| 4,652,428 | 3/1987 | Maruhashi et al. . |
| 4,660,559 | 4/1987 | McGregor et al. . |
| 4,799,484 | 1/1989 | Smith et al. . |
| 4,824,492 | 4/1989 | Wright . |
| 4,846,904 | 7/1989 | Arai et al. . |
| 4,849,166 | 7/1989 | Hoshino et al. . |
| 4,901,722 | 2/1990 | Noguchi . |
| 4,925,500 | 5/1990 | Kishida et al. . |
| 4,961,793 | 10/1990 | Kishida et al. . |
| 4,975,131 | 12/1990 | Honkura et al. . |
| 5,000,912 | 3/1991 | Bendel et al. . |
| 5,023,049 | 6/1991 | Norstrom et al. . |
| 5,035,855 | 7/1991 | Utsunomiya et al. . |
| 5,066,547 | 11/1991 | Ishida . |
| 5,087,415 | 2/1992 | Hemphill et al. . |
| 5,152,774 | 10/1992 | Schroeder . |
| 5,231,771 | 8/1993 | Samsel . |

FOREIGN PATENT DOCUMENTS

| | | |
|---|---|---|
| 0294210 | 12/1988 | European Pat. Off. . |
| 62-101236 | 5/1987 | Japan . |
| 3-80869 | 4/1991 | Japan . |
| 3-118049 | 5/1991 | Japan . |
| 3-118050 | 5/1991 | Japan . |
| WO93/07303 | 4/1993 | WIPO . |

OTHER PUBLICATIONS

Steels: Heat Treatment and Processing Principles, George Krauss (1990).
Stainless Steel, J. Gordon Parr and Albert Hanson (1986), (Revised by R. A. Lula).
Standard Test Methods for Bend Testing of Metallic Flat Materials for Spring Applications Involving Static Loading (ASTM) (May 1990).
A. Hultin Stigenberg and J. O. Nilsson, Corrosion resistant maraging steel for use in medical and dental equipment, Publication of AB Sandvik Steel, Mar. 1992.
Wrought Stainless Steels, Metals Handbook 10th Edition, vol. 1, pp. 841–907 (1990).
Stigenberg Nilsson, Liu and Wilson, The Aging Behavior in a 12Cl-9N:-4Mo Managing Steel used in Dental and Medical Instruments, Oct. 11, 1993.

*Primary Examiner*—Deborah Yee

[57] ABSTRACT

Surgical needles are produced from martensitic precipitation-hardening stainless steel and then vacuum heat treated and vacuum cooled to increase its tensile strength while retaining the polished surface of the needle. A needle made by this process is also disclosed.

20 Claims, 6 Drawing Sheets

METHOD OF MAKING HEAT TREATED STAINLESS STEEL NEEDLES

FIELD OF THE INVENTION

This invention relates generally to materials and methods for making needles. More specifically, this invention relates to vacuum heat treated surgical needles made from precipitation hardening stainless steel and methods for their manufacture.

BACKGROUND OF THE INVENTION

The production of needles involves many processes and different types of machinery to prepare quality needles from raw stock. These varying processes and machinery become more critical in the preparation of surgical needles where the environment of intended use is in humans or animals. Some of the processes involved in the production of surgical grade needles include inter alia: straightening spooled wire stock, cutting needle blanks from raw stock, tapering or grinding points on one end of the blank, providing a bore for receiving suture thread at the other end of the blank, flat pressing a portion of the needle barrel to facilitate easier grasping by surgical instrumentation, and curving the needle where curved needles are desired. Generally, extreme care must be taken to ensure that only the intended working of the needle is performed and that the other parts of the needle remain undisturbed.

The strength of the material used to fabricate the needle will, of course, affect the ultimate strength of the needle. The ultimate strength of a curved surgical needle is normally expressed in terms of the tensile strength and bend moment of the needle. By fabricating a needle from a higher strength material, a smaller diameter needle is required to achieve a desired strength. A reduced diameter needle is desirable, since the smaller the diameter of the needle, the less trauma is caused to the tissue through which the needle passes.

Surgical needles have been made from a variety of stainless steels, including 300 series stainless steels (such as, for example, 301, 302 and 304 stainless steel) and 400 series stainless steels (such as, for example, 420 and 455 stainless steel). Other alloys employed in surgical needle manufacture include those described in U.S. Pat. Nos. 5,000,912 and 1,942,150 and in European Patent Application No. 0 294 210.

In general steel making, 455 steel is an example of a precipitation hardening steel. As disclosed in Stainless Steel, R. A. Lula, 25 (1986) (American Society for Metals), the phenomenon of precipitation hardening is most familiar in aluminum alloys. The general principle is to produce a supercooled solid solution from which, on aging, compounds precipitate. Just as it is possible to supercool a liquid solution of salt in water, by cooling it rapidly and carefully, so it is possible to produce a supercooled solid solution. Hence, at room temperature we have a solid solution that is not stable, but mestastable: there are more alloying element atoms in solution than the structure can really put up with. Given the chance, the structure will induce these atoms to form a separate phase. The chance is offered by time and it may be made more attractive by heat.

During the early stages of the precipitation process, the unwelcome atoms move out of the crowded structure and begin to combine with other atoms about them. Eventually they will form precipitates visible under the microscope, but it is during the early stages (before we can readily see what is going on) that the greatest strength increase occurs—during what is called the preprecipitation stage. When visible precipitates have formed, the strength is usually on the decline, and the alloy is said to have overaged.

The precipitates associated with the hardening process are complex. It is, however, easier to state that in the precipitation-hardening stainless steels, additional elements (aluminum, molybdenum, copper) that are active in the precipitation-hardening process are introduced, and heat treatments are devised to produce first the supersaturated solid solution and then the preprecipitation stage.

Prior steel treatments have deficiencies. Hardening the steel in wire form, as in U.S. Pat. No. 5,000,912, makes it more difficult to shape into needles. EP 294210 discloses vacuum heat treating needles of a high cobalt-steel alloy and then cooling them in air.

SUMMARY OF THE INVENTION

A difficulty in making surgical needles is to make sufficiently hard needles. However, to shape needle blanks having this desired hardness is difficult. The present invention overcomes these difficulties by shaping soft needle blanks and then hardening the finished needles. The present invention achieves this by making surgical needles of superior tensile strength from martensitic precipitation-hardening stainless steel materials. In accordance with the present invention, a needle blank is cut from a stock wire and the needle blank shaped (drilled, grinded, pressed, curved, etc.) into a surgical needle. After shaping, the needles are heated under vacuum and cooled in the absence of oxygen, i.e., absence of air, preferably at least in part under vacuum, to increase their tensile strength. By this process, higher strength needles can be manufactured compared to those formed from wire which has not been so treated. The vacuum for heat treating, and absence of oxygen for cooling, avoids the need to polish the heat treated needles. This preserves the sharp point and edges put on the needle before treating and avoids having to resharpen the needle hardened by heat treating. Another advantage is that because the needles are shaped before hardening, they can be hardened to their peak hardness without making shaping difficult. The needles may be straight or curved, but this ability to peak harden is especially advantageous for curved needles.

DESCRIPTION OF PREFERRED EMBODIMENTS

Surgical needles are manufactured, in accordance with the present invention, from stock wire manufactured from a martensitic precipitation-hardening stainless steel. Preferably, such steel has at least 50% of the martensitic phase, more preferably at least 70% of the martensitic phase.

The precipitation hardening steels obtain high strength in a stainless steel by a low temperature treatment applied after shaping the needle. This low temperature treatment is known as aging. Aging has different effects on different types of steel. For example, contrary to the steels employed in the present invention, heat treatment of austenitic steels does not cause hardening. Perry's Chemical Engineer's Handbook, 6th Ed., p. 23–40 (1984). It merely reduces stresses induced by cold working the steel.

The general and specific compositions of preferred martensitic precipitation-hardening stainless steels are as shown on Table I:

6%, cobalt up to about 6%, copper between about 0.5% to about 4%, aluminum added up to about 0.6%, titanium between about 0.4% and about 1.4%, carbon and nitrogen not exceeding about 0.05%, with iron as the remainder and the content of any other element of the periodic table not exceeding about 0.5%. Preferably, the alloy has about 0.5% to about 3% copper, up to about 6% cobalt, and about 0.5% to about 4.5% molybdenum. More preferably, the alloy has up to about 3% cobalt. Most preferably, this stainless steel comprises about 11.5 to about 12.5 weight percent chromium, about 8.5 to about 9.5 weight percent nickel, about 0.8 to about 1.0 weight percent titanium, about 3.5 to about 4.5 weight percent molybdenum, about 0.5 to about 2.5 weight percent copper, up to about 0.02 weight percent carbon, up to about 0.5 weight percent manganese, up to about 0.5 weight percent silicon, up to about 0.20 weight percent sulfur, with the remainder consisting essentially of iron. A preferred martensitic precipitation-hardening alloy for use in the present invention is 1RK91 TM steel, developed by A. B. Sandvik Steel, S-811 81 Sandviken, Sweden.

TABLE I

| | WEIGHT PERCENTS | | | | | | | | |
|---|---|---|---|---|---|---|---|---|---|
| ELEMENT | GENERAL COMPO- SITION | PREFERRED COMPO- SITION | CARPENTER 455 | STAIN- LESS W | 17-4 PH | 15-5 PH | PH 13 MO | CUSTOM 450 | SANDVIK 1RK91 |
| Fe | Balance | Balance | Balance | Balance | Balance | Balance | Balance | Balance | Balance |
| Cr | 10–17 | 11–13 | 11.0–12.5 | 16.5 | 16.0 | 15.0 | 12.5 | 15.0 | 11.7 |
| Ni | 4–11 | 7–10 | 7.5–9.5 | 6.75 | 4.0 | 4.0 | 8.0 | — | 9.1 |
| Ti | 0–1.6 | 0.8–1.4 | 0.8–1.4 | 0.8 | — | — | — | — | 1.0 |
| Mo | 0–6 | 0.5–4.5 | 0.50 | — | — | — | 2.5 | 1.0 | 4.1 |
| Cu | 0–4 | 1–3 | 1.5–2.5 | — | 3.2 | 4.0 | — | 0.75 | 2.0 |
| C | <0.02–0.07 | 0.015–0.06 | 0.05 | 0.07 | 0.04 | 0.07 | 0.05 | 0.05 | .004 |
| Mn | 0.5–0.6 | <0.5–0.6 | 0.50 | 0.5 | 0.25 | — | 0.5 | — | .17 |
| Si | <0.5–1 | <0.5–0.6 | 0.50 | 0.5 | 0.60 | — | 0.5 | 1.0 | .05 |
| P | 0–0.2 | 0–0.04 | 0.04 | — | — | 0.20 | — | — | — |
| S | 0–0.04 | 0–0.04 | 0.03 | — | 0.01 | — | — | — | .002 |
| Nb | 0–0.5 | 0–0.5 | 0.10–0.50 | — | — | — | — | 0.40 | — |
| Ta | — | — | — | — | — | — | — | — | — |
| Al | 0–1.1 | 0 | — | 0.4 | — | — | 1.1 | — | — |
| Nb + Ta | 0–0.6 | 0 | — | — | 0.25 | 0.35 | — | — | — |
| Cb(min) | 0–8xC | 0 | — | — | — | — | — | 8xC | — |
| Cobalt | 0–6 | 0–3 | — | — | — | — | — | — | — |

Most preferably, the alloys contain a nickel-titanium ($Ni_3$—Ti) precipitation hardening phase. Preferably, such an alloy contains about 4 to about 11 weight percent nickel and about 0.0 to about 1.6 weight percent titanium, more preferably about 7 to about 10 weight percent nickel and about 0.8 to about 1.4 weight percent titanium.

A preferred alloy is 455 steel. This 455 stainless steel contains about 11 to about 12.5 weight percent chromium, about 7.5 to about 9.5 weight percent nickel, about 0.8 to about 1.4 weight percent titanium, about 0.5 to about 0.7 weight percent molybdenum, about 1.5 to about 2.5 weight percent copper about 0.04 to about 0.06 weight percent carbon, about 0.4 to about 0.6 weight percent manganese, about 0.4 to about 0.6 weight percent silicon up to about 0.04 weight percent phosphorus, about 0.02 to about 0.04 weight percent sulfur, about 0.1 to about 0.5 weight percent niobium, with iron as the remainder.

A class of precipitation hardenable alloys are disclosed by PCT Application WO 93/07303, incorporated herein by reference. This PCT application discloses a precipitation hardenable martensitic stainless steel alloy comprising, in percent by weight, about 10% to about 14% chromium, between about 7% to about 11% nickel, molybdenum between about 0.5% to about The stock wire can be provided in any diameter suitable for needle manufacture. Normally the diameter of the wire is between about 0.001 and about 0.075 inches. The hardness and tensile strength of the stock wire will depend on the diameter of the wire, its composition and the processes employed in making the stock wire.

Figure 3:
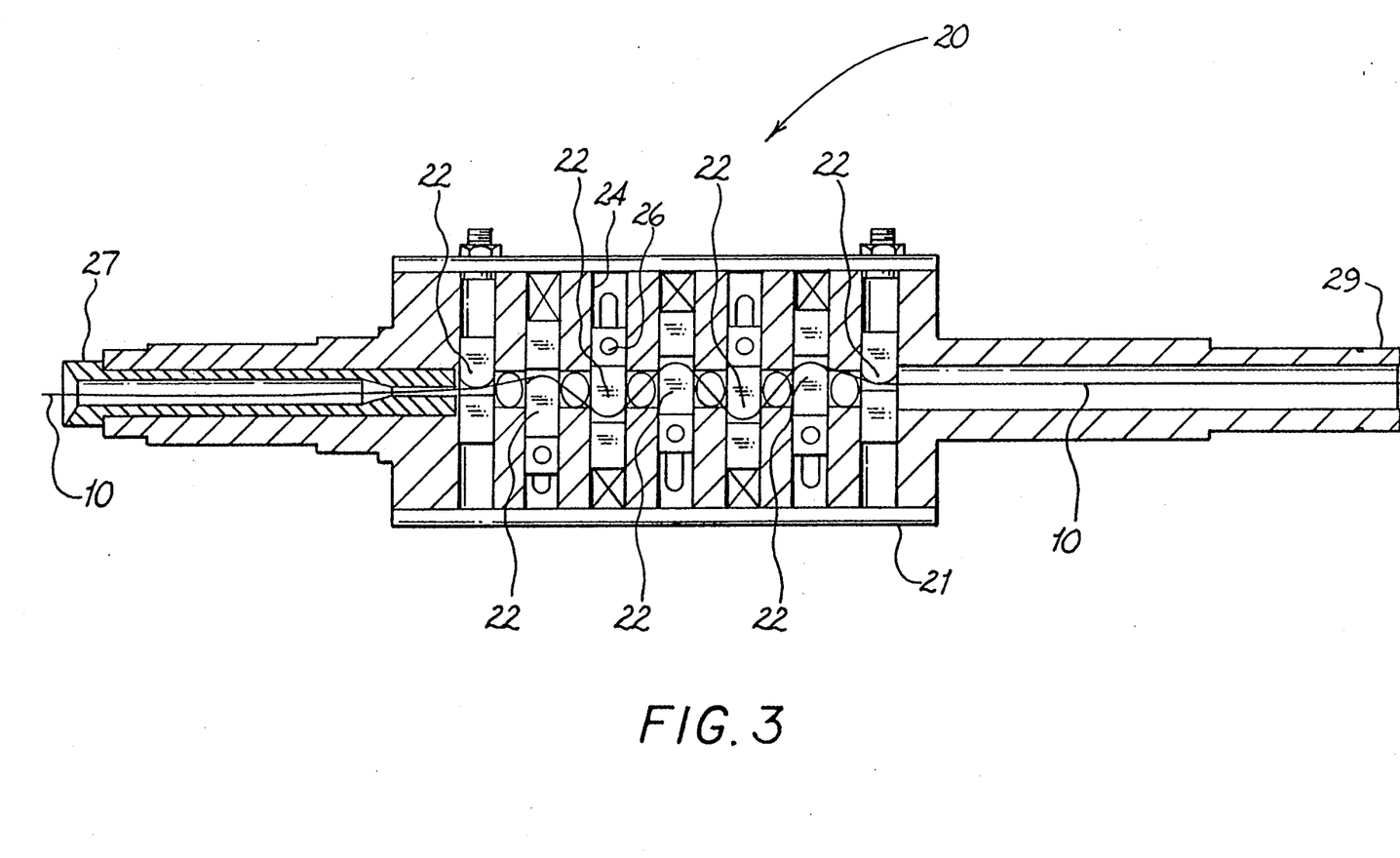
FIG. 3 is a plan view of a wire straightening device useful in the present invention.

Normally, stock wire for needle manufacture is supplied in a coil and requires straightening before needle blanks can be cut therefrom. Any conventional wire straightening device may be employed straighten the stock wire. One such device is shown in FIG. 3 and generally denoted by the numeral 20. The straightener includes housing 21 and interdigitating dies 22. Stock wire 10 is positioned adjacent the inner face of each die 22. Each die 22 is located in a channel 24 within housing 21. The position of each die 22 within the housing 21 may be adjusted by loosening set screw 26.

In operation, once the wire 10 is threaded through the straightener 20 as shown, the entire housing of the straightener is rotated at speeds up to 4,000 rpm, while the wire is pulled therethrough at a rate in the range 0.1 to 30 feet per minute. When the wire 10 exits end 29 of straightener 20, it no longer has any curl which may have been imparted to the wire during coiling or storage in the coiled state. Ascertaining the appropriate number and positioning of dies 22 required to straighten a wire of a particular diameter and composition is within the purview of chose skilled in the art. A particularly useful straightener is that disclosed in co-pending application entitled APPARATUS FOR STRAIGHTENING COILED WIRE, U.S. Ser. No. 07/959,059, filed on Oct. 9, 1992.

Preferably, the stock wire is cleaned, for example by ultrasonic cleaner prior to being threaded through the straightener. This cleaning will remove any debris which might interfere with accurate and smooth handling of needle blanks formed from the stock wire.

Figure 4:
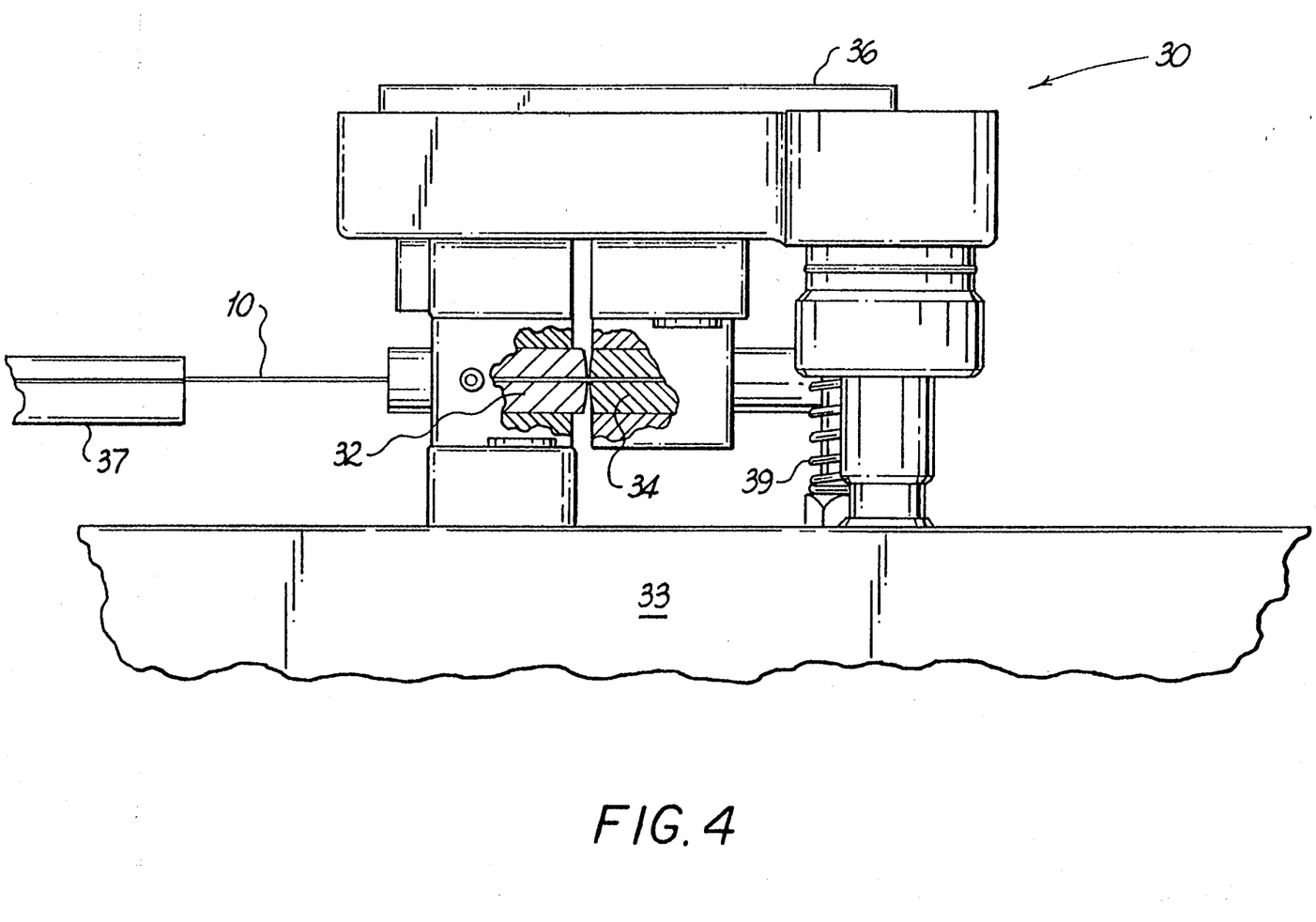
FIG. 4 is a side elevation view of a wire cutting device with portions cut away to show the internal structure thereof.

Once cleaned and straightened, the stock wire can be cut into needle blanks. Cutting of the needle blanks can be achieved by any suitable means. One suitable wire cutting device 30, shown in FIG. 4, includes a stationary die 32, mounted to base 33 and a moveable die 34 mounted on strike plate 36. Stock wire 10 passes through a central bore in each die 32, 34. The diameter of the bores in dies 32, 34 is only slightly greater than the diameter of stock wire 10, preferably with a tolerance of no more than 0.001 inches. The dies 32, 34 are removable and can be replaced with different size dies to accommodate different size wires. In operation, a stepper motor 37 advances the stock wire 10 a predetermined distance, which distance corresponds to the length of the needle blank to be formed. Once the stock wire is properly positioned, press means (not shown) is activated which hits strike plate 36. The press means may be of any conventional type and should be capable of developing a force in the range of 3 to 30 tons. Preferably an electro-mechanical press is used. When strike plate 36 is struck, moveable die 34 moves quickly and suddenly downward, thereby shearing stock wire 10 at the interface of dies 32, 34. Spring 39 pushes the strike plate 36 back to its original position and stepper motor 37 advances stock wire 10 another increment thereby expelling the needle blank from the moveable die. The distance moveable die 34 moves is preferably no more than 0.0001 to 0.005 inches greater than the diameter of the stock wire 10. The length of the needle blank can range from 1 to 2.5 times the length of the finished needle. Preferably, the needle blank is cut to a length of 1 to 1.1 times the length of the finished needle so that no additional cutting step is required to trim the needle blank to its final length.

After the stock wire is cut into a needle blank, the various operations necessary for shaping the needle blank into a surgical needle can be performed. The operations performed will depend on the type of needle being produced. One sequence of needle shaping and preparation steps is shown schematically in FIG. 2. The steps set forth in FIG. 2 will provide a curved, rectangular bodied needle optionally with cutting edges. While the steps of shaping the needle blank into a surgical needle will herein be described with respect to the steps set forth in FIG. 2, it should be understood that steps other than those shown in FIG. 2 may be employed and that the order of the steps may be changed from the order shown in FIG. 2. Alternatively, some of the steps shown in FIG. 2 may, if desired be eliminated. For example, where a straight needle is desired, the curving step may be eliminated. Other variations will be apparent to those skilled in the art. In addition, while specific devices are described herein for performing the needle blank forming and shaping steps, the invention is not limited to the specific devices disclosed. Other devices may be employed or the devices disclosed may be combined, for example, by mounting on a common frame member, to provide a device capable of performing a plurality of the steps.

Figure 1:
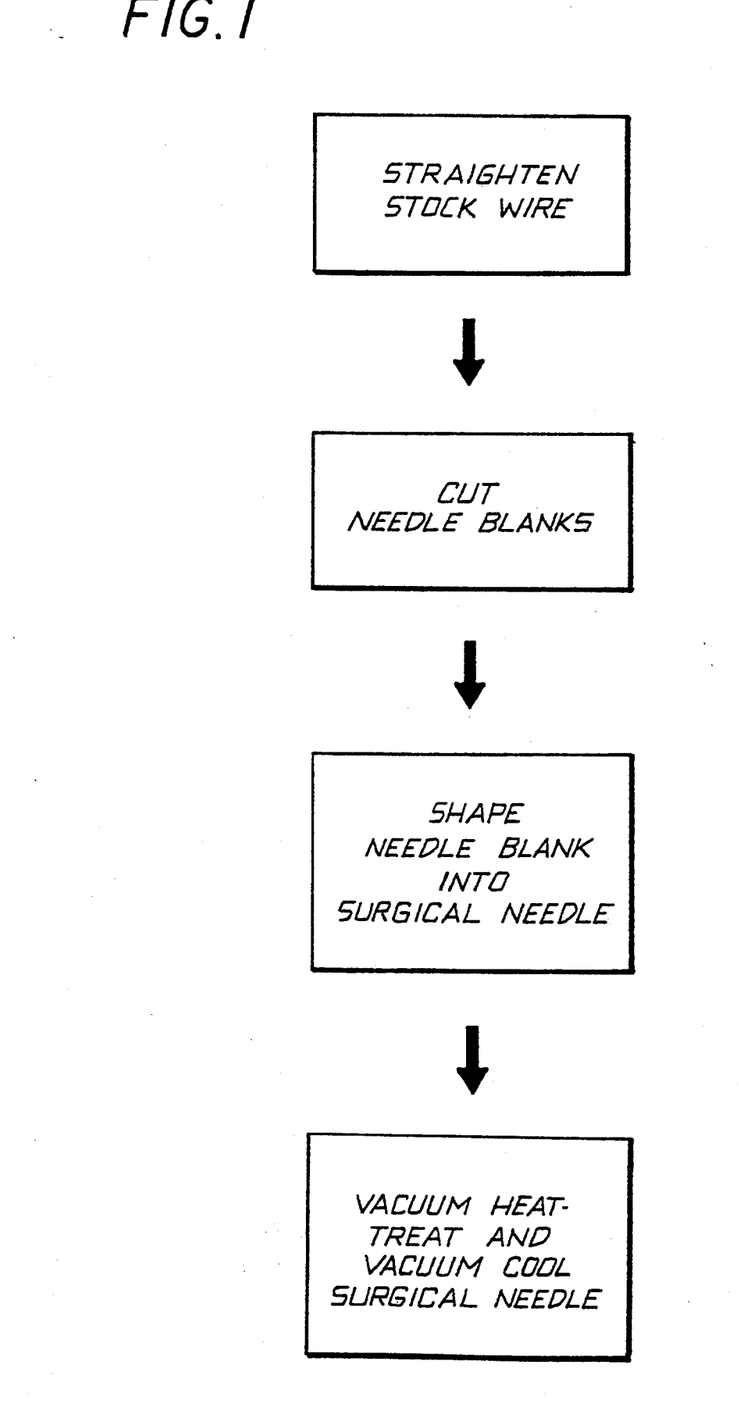
FIG. 1 is a flow diagram showing the steps of a needle making method in accordance with the present invention.
Figure 2:
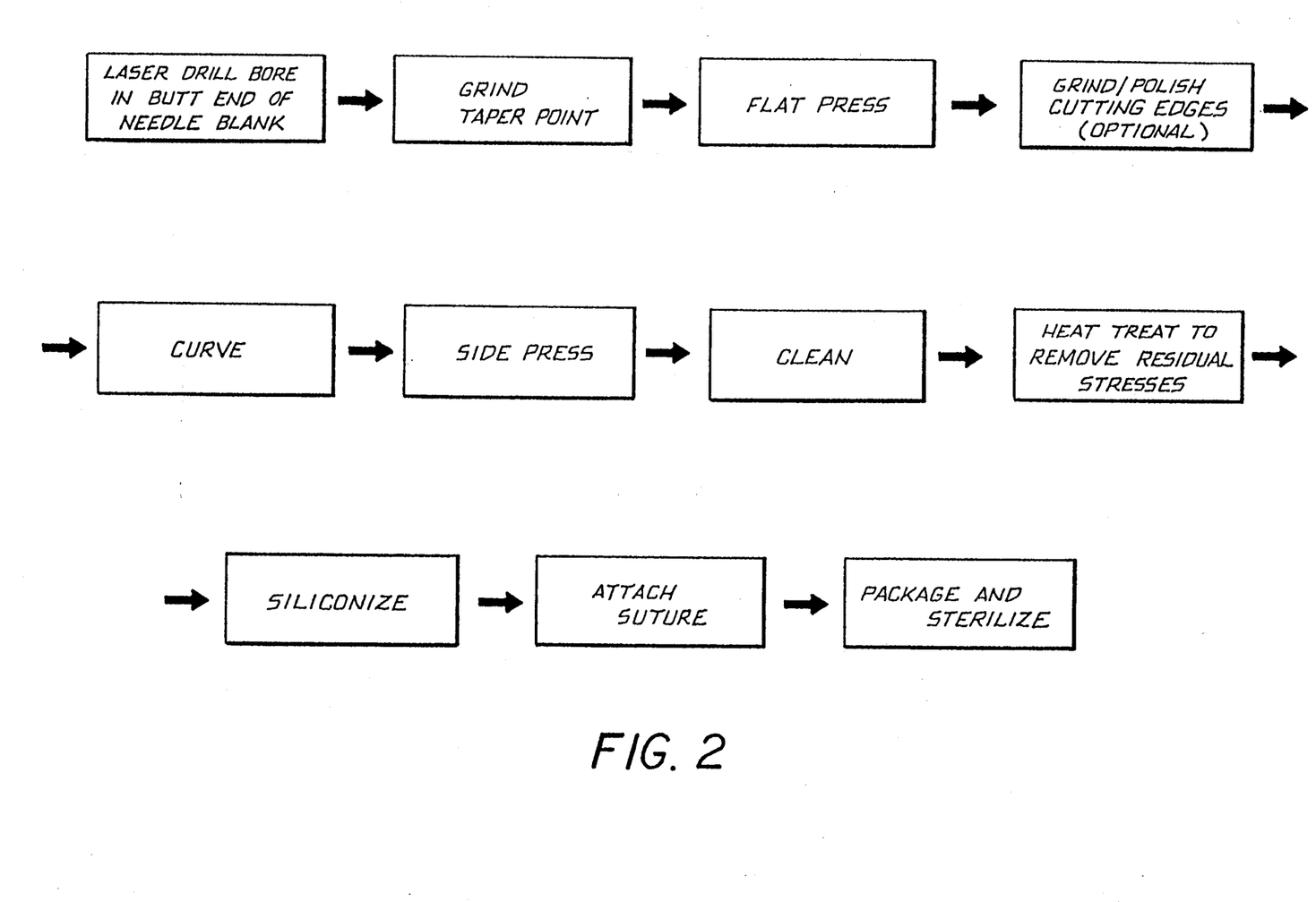
FIG. 2 is a flow diagram showing the steps of a shaping process for use in the present invention for preparing curved, rectangular bodied needles.

As shown in FIG. 2, the first step in forming the needle from the needle blank is to laser drill a bore in one end of the needle blank. The bored end of the blank will hereinafter be referred to as the butt end of the needle. The bore is provided for attaching a suture thread to the needle. While any type of suture attachment means may be formed in the needle blank, a bore is the preferred suture attachment means. In addition, the bore may be formed using any known techniques such as mechanical drilling, electric discharge machining and electron beam machining. However, laser drilling is the preferred technique for providing the bore.

Drilling the bore on a straight piece of wire of uniform diameter is advantageous since precise positioning of the needle blank is required for laser drilling. Achieving the precise positioning required for laser drilling is far easier with a straight wire of uniform thickness than for tapered or curved workpieces. A particularly preferred device for positioning needle blanks for laser drilling is that disclosed in co-pending application entitled NEEDLE BLANK FEEDING APPARATUS, U.S. Ser. No. 07/951,394 filed on Sep. 25, 1992, the disclosure of which is incorporated herein by reference.

Figure 5A:
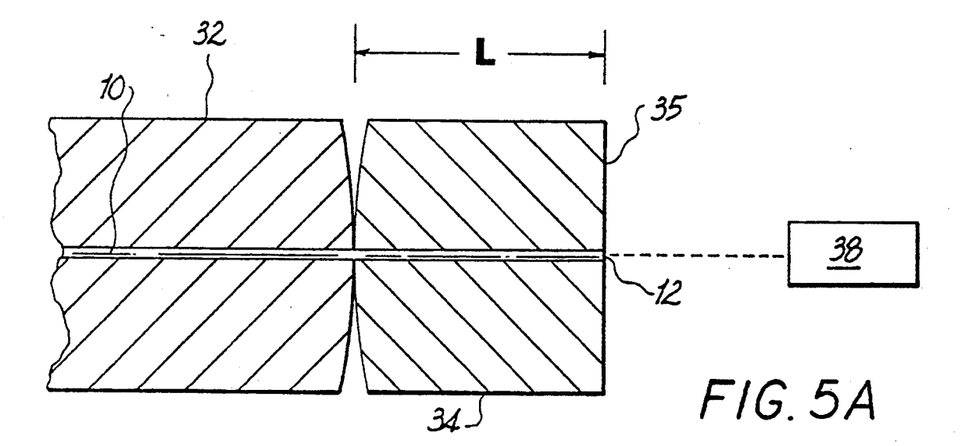
FIGS. 5A-C schematically show the steps of a process in accordance with a further aspect of the present invention.
Figure 5B:
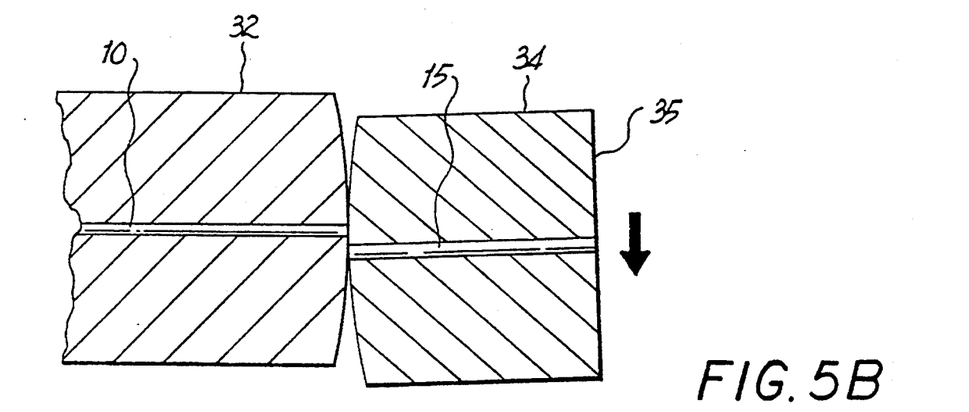
Figure 5C:
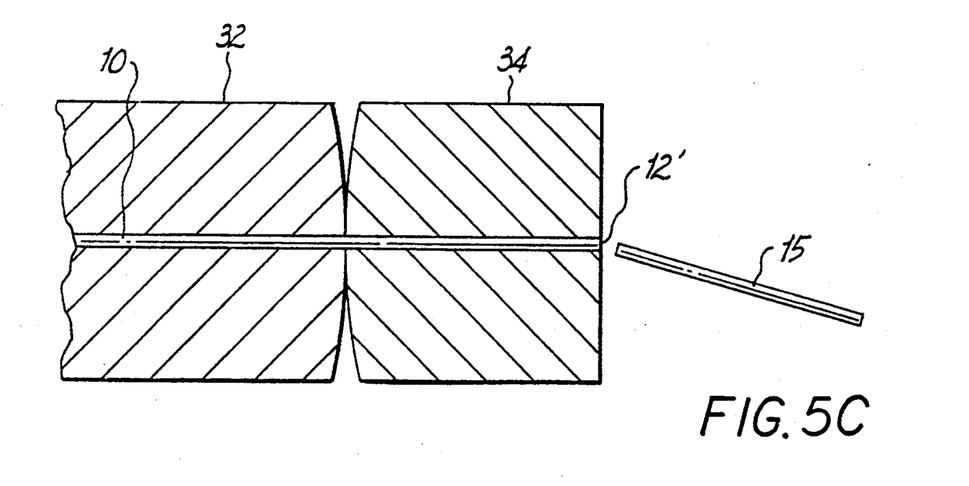

When the stock wire diameter is less than 0.016 inches, the end of the stock wire may advantageously be laser drilled prior to the cutting of the needle blank. This can be accomplished by making the moveable die in the device of FIG. 4 have the same length "L" as the needle blank to be formed and positioning a laser so that the beam travels directly along the longitudinal axis of the bore on the moveable die. The stepper motor advances the stock wire 10 so that face end 12 thereof is at the exit face 35 of moveable die 34, as shown in FIG. 5A. The laser is then actuated to apply the laser beam to the face end 12 of stock wire 10. After the laser fires, the press means are activated to cut the stock wire 10 at the interface of the fixed and moveable dies 32 and 34, respectively, as shown in FIG. 5B. The stepper motor then advances the stock wire 10 to eject the drilled needle blank 15 from the moveable die and present the new end 12' of the stock wire 10 for drilling.

A taper point may be provided on the needle blank using any known techniques. Automatic point grinding devices such as those manufactured by Schumag-Machinery Inc. Norwood, N.J. are suitable for applying taper points to the needle blanks. Conventional bonded grinding wheels may be employed. However, when forming needles in accordance with the present invention, the grinding wheel is preferably of the electroplated type having a pre-shaped, pre-dressed core made of aluminum or other suitable material and plated with a superabrasive such as cubic boron nitride which is available from the General Electric Company under the tradename Borazon. Such grinding wheels are more durable than conventional wheels. Obviously, other known abrasive materials may be substituted for Borazon, such as, for example, aluminum oxide ($Al_2O_3$) or silicon carbide (SiC).

A particularly preferred automatic taper grinding machine is that disclosed in co-pending application entitled APPARATUS AND METHOD FOR GRINDING POINTS, U.S. Ser. No. 07/959,054, filed on Oct. 9, 1992, the disclosure of which is incorporated herein by reference.

The pointed needle blank can be flat pressed using conventional pressing devices, such as, for example, a 5 or 10 ton press, to provide two flattened surfaces along the body of the needle blank between the butt end and the taper point. Flat sides on a needle facilitate grasping of the needle by the forceps-like needle holders employed during surgical procedures. Care must be taken during the flat press step not to position the butt end or any cutting edges formed on the needle blank directly between the dies of the press. The dies used to flat press may be conformed to provide conventional runouts between the body of the needle and both the butt end and pointed end of the needle blank.

Cutting edges can then optionally be provided on the flattened, pointed needle blank using conventional techniques. As with the taper point grinding, grinding belts or wheels carrying superabrasives are preferably employed to apply the cutting edges. Cutting edges can be provided on the needle blank using the device disclosed in co-pending U.S. application entitled APPARATUS FOR APPLYING A CUTTING EDGE TO A NEEDLE, U.S. Ser. No. 07/959,326, filed on Oct. 9, 1992, the disclosure of which is incorporated herein by reference.

The needle blank can then be curved to a desired radius of curvature. Curving can be accomplished by bending the wire around a mandrel. Because the needle blanks made in accordance with this invention are generally springy materials, the surface of the mandrel used for curving should have a tighter curve than that desired in the final needle to allow for some spring back after the bending operation. When the needle blank is flat pressed prior to curving, it is desirable for the flattened side of the needle blank to be positioned against the mandrel to help ensure that uniform curving is achieved. While manual curving may be employed, a preferred curving device will be automated such as the device disclosed in co-pending U.S. application entitled NEEDLE CURVING APPARATUS, U.S. Ser. No. 07/958,926, filed on Oct. 9, 1992, the disclosure of which is incorporated herein by reference.

Once curved, the needle blank can be side pressed to provide a rectangular body section. Side pressing not only further facilitates grasping by a needle holder during surgery, but also provides additional strength to the needle. As with the flat pressing step, care must be taken not to press directly on the butt end of the needle where the suture attachment bore is located. The curved needle may be manually placed between the dies of a conventional press such that the butt end and tapered point section are not located under the dies. Automated machinery for positioning and side pressing the curved needle blank can also be employed. For example, the device disclosed in co-pending U.S. application entitled APPARATUS FOR ORIENTING A CURVED WORKPIECE, U.S. Ser. No. 07/959,050 filed on Oct. 9, 1992, (the disclosure of which is incorporated herein by reference) accurately positions and side presses curved workpieces such as surgical needles.

An increase in the radius of curvature of the needle will occur during side pressing of a curved needle blank formed from stock wire in accordance with the present invention. Accordingly, curving must be done around a mandrel having a surface which is sufficiently smaller than the ultimate curvature desired to account for both the spring back of the material and the increase in curvature resulting from side pressing. Typically, the surface of the mandrel should have a radius of curvature which is from 40 to 60 percent less than the desired final curvature of the needle.

Once side pressed, the needle shaping steps are completed. Then the needles are cleaned and dried. The remaining steps are performed to prepare the needle for use.

First, the needle is subjected to a heat treatment under vacuum. The temperature and duration of heating will vary depending on the composition of the stock material and the shaping operations performed. The heating temperature and time are selected to maximize the bend moment of the surgical needle. Typically, the needle is heated in a vacuum oven at temperatures ranging from about 350° to about 550° C. for periods ranging from about 15 minutes to about 20 hours. Preferably, the needle is heated in a vacuum oven at temperatures from about 400° C. to about 500° C. for about 30 minutes to about 10 hours. Most preferably, temperature ranges from about 400° C. to about 475° C. and the heating time ranges from about 30 minutes to about 90 minutes. Preferably, the vacuum pressure is at most about $1 \times 10^{-3}$ torr, most preferably at most about $1 \times 10^{-4}$ torr. This vacuum may be typically achieved by a diffusion pump.

After heating, the needles are cooled in the oven under vacuum from the heating temperature to a temperature in the range from about 150° C. to about ambient temperature. A typical ambient temperature is about 20° C. The needles may be cooled entirely under vacuum, entirely in the presence of inert, i.e., non-oxidizing, gas, or under vacuum followed by inert gas. The inert gas may speed cooling.

Preferably, the needles are cooled in the oven under vacuum from the heating temperature to a temperature in the range from about 100° C. to about ambient temperature. Most preferably, the needles are cooled under vacuum to a temperature in the range from about 50° C. to about ambient. The needles may cool all the way to ambient under vacuum, or inert gas, preferably nitrogen, is injected into the oven when the oven temperature is above ambient but less than about 150° C., preferably less than about 100° C., most preferably less than about 75° C. Air should not contact the needles until the oven temperature is below about 40° C., preferably below 25° C. Most preferably, nitrogen is flooded into the oven before contact with air, even if the needles are cooled all the way to ambient under vacuum. Cooling under vacuum may take as much as 10 hours but typically takes about 2 to about 5 hours.

In the alternative, the needles are cooled by injecting non-oxidizing gas into the vacuum oven when the oven is at the heating temperature. Such gas has low humidity, preferably it has a dew point less than about −20° C., most preferably less than about −30° C. Typical inert gases are nitrogen, hydrogen, helium, argon, krypton or combinations thereof, such as cracked ammonia which is a combination of hydrogen and nitrogen. Nitrogen is preferred.

Bend moment may be measured by a test similar to ASTM standard E855. ASTM standard E855 is employed with flat springs rather than needles. An apparatus for accurate measurement of bend moment is disclosed by U.S. Pat. No. 5,022,273, incorporated herein by reference. By virtue of the present invention, preferably bend moment for a 455 steel or 1RK91 ™ steel needle having a 12 mil diameter is about 75 to about 100 gm.cm or about 100 to about 125 gm.cm., respectively. Preferably bend moment for a 455 steel or 1RK91 ™ steel needle having a 28 mil. diameter is about 800 to about 1050 gm.cm. and about 1100 to about 1350 gm.cm., respectively. The heating and cooling process described herein increases bend moment by about 10% to about 60% without tarnishing the needle.

After heat treating and cooling, the needles are cleaned, dried and siliconized if desired. A process for siliconization is disclosed by Siliconized Surgical Needle And Method For Its Manufacture, U.S. patent application Ser. No. 08/023,734 incorporated herein by reference. A suture can then be inserted into the bore at the butt end of the needle and secured to the needle by crimping, swaging or other processes. The needled suture can then be packaged and sterilized.

The following examples illustrates the advantages achieved by the present invention.

EXAMPLE 1

| 0.028" diameter Carpenter 455 |
| --- |
| Before Precipitation Heat Treatment |
| Wire 190,000 psi tensile strength |
| Needles 600 g · cm 2 degree offset yield bend moment |
| After precipitation heat treatment under vacuum ($1 \times 10^{-5}$ torr.), at 475° C. for 4 hours and cooling under vacuum for 4.5 hours to 30° C. before injection of nitrogen to further cool to ambient temperature: |
| Wire 290,000 psi tensile strength |
| Needles 900 g · cm 2 degree offset yield bend moment |

EXAMPLE 2

Materials such as 1RK91 TM steel can be heat treated by the present invention to tensile strengths above 400,000 psi and of about 1200 g.cm 2 degree offset bend moment for 0.028 inch diameter wire and needle, respectively, by procedures such as that of Example 1.

EXAMPLE 3

Figure 6:
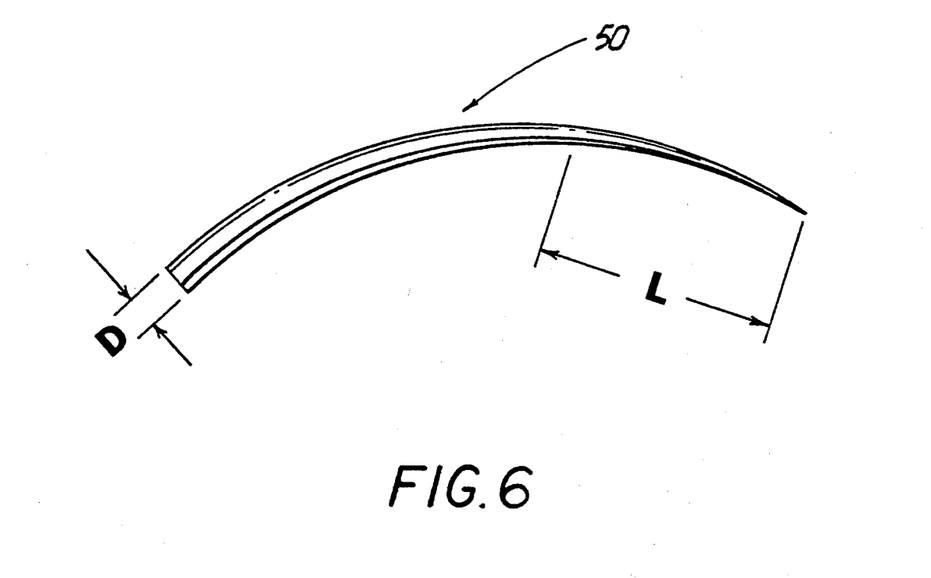
FIG. 6 is a schematic drawing of an embodiment of a surgical needle of the present invention.

Heating and cooling under vacuum results in needles retaining their polished finish. This avoids a repolishing step. Thus, a major advantage of the present invention is that it results in strong sharp needles. Typically a curved 12±1 mil diameter needle 50 having a taper point configuration of FIG. 6 wherein the taper "T" to diameter "D" ratio ranges from about 6:1 to about 16:1 (preferably from about 8:1 to about 16:1), made of 1RK91 TM steel and treated according to the present invention followed by siliconization had a bend moment of about 110 gm. cm. Also, such a needle 50 has a needle penetration force through 0.017 inch Porvair TM material of less than about 35 grams force (preferably less than about 25 grams force). Such a needle made of 455 steel would be expected to have a bend moment of about 85 g.cm. and essentially the same penetration force. Porvair TM materials consist of a homogenous 100% polyester polyurethane microporous structure, containing no free plasticizers. Porvair TM material is available from Porvair PLC, 35 Estualy Road, King's Lynn, Norfolk, U.K. PE302HS through Marand Marketing International, Inc., 18 South Main Street, Topsfield, Mass 01983, U.S.A.

EXAMPLE 4

Figure 7:
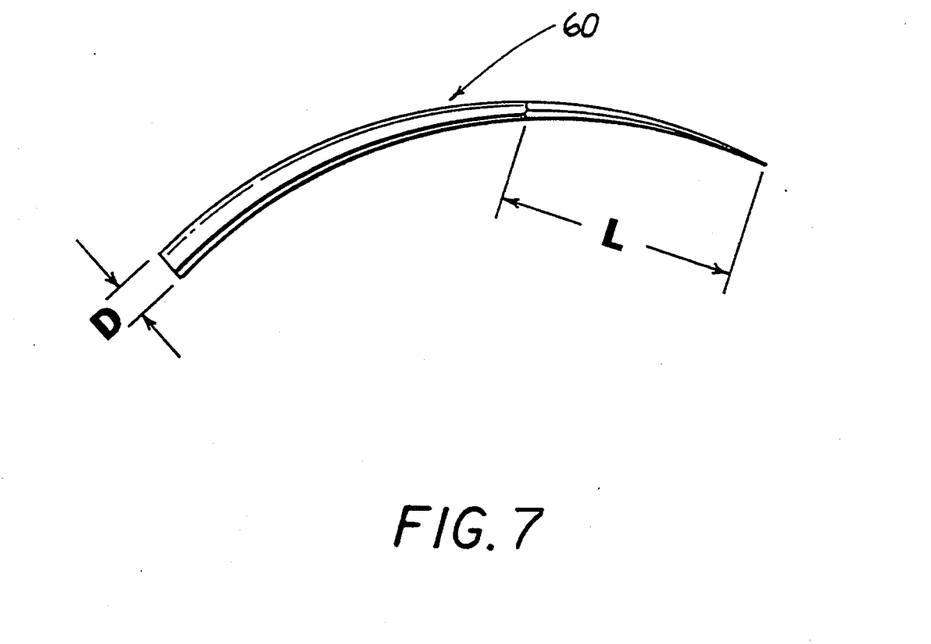
FIG. 7 is a schematic drawing of a second embodiment of a surgical needle of the present invention.

Typically, a curved 28±1 mil needle 60 having the taper cut needle configuration of FIG. 7 wherein the taper "T" to diameter "D" ratio ranges from about 6:1 to about 16:1, (preferably from about 8:1 to about 16:1) made of 455 steel and treated according to the present invention followed by siliconization had a bend moment of about 900 gm.cm. Also, such a needle 60 has a needle penetration force through 0.044 inch thick PERMAIR model of Porvair TM materials of less than about 200 grams force, preferably less than about 150 grams force. Such a needle made of 1RK91 TM steel would have a bend moment of about 1200 gm.cm. and essentially the same penetration force. PERMAIR materials consist of homogeneous aromatic polyester urethane microporous structure, containing no free plastisizers. PERMAIR material is available from Porvair PLC, 35 Estualy Road, King's Lynn, Norfolk, U.K. PE302HS through Marand Marketing International, Inc., 18 South Main Street, Topsfield, Mass. 01983, U.S.A.

A procedure for measuring needle penetration is disclosed by Apparatus And Method For Testing Point Sharpless Of Needles, U.S. Pat. No. 5,181,416, incorporated herein by reference. Additional background is provided by Thacker, et al., "Surgical Needle Sharpness", American Journal of Surgery, No. 157, pp. 334–339 (1989), also incorporated herein by reference.

EXAMPLE 5

Table II lists typical bend moments achieved by heat treating and cooling essentially as in EXAMPLE 1.

TABLE II

| Bend Moment g.cm. | | |
| --- | --- | --- |
| 455 | RK91 TM | Wire (mils) |
| — | 55 | 10 |
| — | 110 | 12 |
| 150 | 180 | 15 |
| 900 | 1200 | 28 |
| 2300 | — | 39 |
| 6500 | — | 62 |

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

We claim:

1. A process for using martensitic precipitation hardening stainless steel to make surgical needles comprising the steps of:

forming needle blanks consisting essentially of martensitic stainless steel into surgical needles by at least one step selected from the group consisting of sharpening a first end to be pointed, tapering, bending, and drilling a hole into a second end of said needle blank;

heating said surgical needles under vacuum at a temperature in the range from about 350° C. to about 550° C. for a time in the range from about 15 minutes to about 20 hours;

cooling said heated surgical needles in the absence of oxygen from said heating temperature to a temperature in the range from about 150° C. to about ambient temperature, whereby said heating step hardens the surgical needle subsequent to said forming step.

2. The process of claim 1, wherein said martensitic precipitation-hardening stainless steel comprises about 10 to about 17 weight percent chromium, about 4 to about 11 weight percent nickel, up to about 1.6 weight percent titanium, about 0 to about 6 weight percent molybdenum, up to about 4 weight percent copper, up to about 6 weight percent cobalt, up to about 1.1 weight percent aluminum, at most about 0.07 weight percent total for carbon and nitrogen, up to about 0.6 weight percent manganese, up to about 1 weight percent silicon, up to about 0.2 weight percent phosphorous, up to about 0.04 weight percent sulfur, up to about 0.5 weight percent niobium, up to about 0.6 weight percent total niobium plus tantalum, with the remainder consisting essentially of iron.

3. The process of claim 2, wherein said heated surgical needles are cooled under vacuum to a temperature in the range from about 150° C. to about ambient temperature and said heating and cooling occur at a vacuum pressure of at most about $1 \times 10^{-3}$ torr and said heating temperature is in the range from about 400° C. to about 500° C. and said heating time is in the range from about 30 minutes to about 10 hours.

4. The process of claim 2, wherein said cooling occurs over a time from about 2 hours to about 5 hours and said heating time is in the range from about 30 minutes to about 90 minutes, and said heating temperature is in the range from about 400° C. to about 475° C.

5. The process of claim 2, wherein said cooling step further comprises contacting said cooled needles at a temperature in the range from about 150° C. to about ambient with inert gas prior to exposing said cooled needles to oxygen.

6. The process of claim 2, wherein said heating and cooling occur under vacuum maintained at a pressure of at most about $1 \times 10^{-4}$ torr and said needles are cooled under said vacuum to a temperature in the range from about 100° C. to about ambient.

7. The process of claim 1, wherein the times and temperature or said heating step are selected to maximize the bend moment of said surgical needle.

8. The process of claim 1, wherein said heating and cooling increases bend moment by about 10 percent to about 60 percent without tarnishing said needle.

9. The process of claim 1, wherein said cooling step occurs in the presence of inert gas.

10. The process of claim 9, wherein said inert gas is nitrogen.

11. The process of claim 1, wherein said stainless steel comprises a nickel-titanium precipitation phase and at most about 0.05 weight percent of cobalt.

12. The process of claim 1, wherein said stainless steel comprises at least 50 weight % of a martensite phase.

13. The process of claim 1, wherein said stainless steel comprises about 11.0 to about 13 weight percent chromium, about 7 to about 10 weight percent nickel, about 0.8 to about 1.4 weight percent titanium, about 0.5 to about 4.5 weight percent molybdenum, about 1 to about 3 weight percent copper, about 0.015 to about 0.06 weight percent carbon, up to about 0.6 weight percent manganese, up to about 0.6 weight percent silicon, up to about 0.04 weight percent phosphorous, up to about 0.04 weight percent sulfur, up to about 0.50 weight percent niobium, with the remainder consisting essentially of iron.

14. The process of claim 1, wherein said stainless steel comprises about 11 to about 12.5 weight percent chromium, about 7.5 to about 9.5 weight percent nickel, about 0.8 to about 1.4 weight percent titanium, about 0.5 to about 0.7 weight percent molybdenum, about 1.5 to about 2.5 weight percent copper, about 0.04 to about 0.06 weight percent carbon, about 0.4 to about 0.6 percent weight percent manganese, about 0.4 to about 0.6 weight percent silicon, up to about 0.04 weight percent phosphorous, about 0.02 to about 0.04 weight percent sulfur, about 0.1 to about 0.5 weight percent niobium, with the remainder consisting essentially of iron.

15. The process of claim 1, wherein said stainless steel comprises a precipitation hardenable martensitic stainless steel alloy comprising, in percent by weight, about 10% to about 14% chromium, between about 7% to about 11% nickel, molybdenum between about 0.5% to about 6%, cobalt up to about 6%, copper between about 0.5% to about 4%, aluminum added up to about 0.6%, titanium between about 0.4% and to about 1.4%, carbon and nitrogen not exceeding about 0.05%, with the remainder consisting essentially of iron.

16. The process of claim 15, wherein said stainless steel comprises about 11.5 to about 12.5 weight percent chromium, about 8.5 to about 9.5 weight percent nickel, about 0.8 to about 1.0 weight percent titanium, about 3.5 to about 4.5 weight percent molybdenum, about 0.5 to about 2.5 weight percent copper, up to about 0.20 weight percent carbon, up to about 0.5 weight percent manganese, up to about 0.5 weight percent silicon, up to about 0.20 weight percent sulfur, with the remainder consisting essentially of iron.

17. The process of claim 1, wherein said stainless steel comprises at least 70 weight percent of a martensite phase.

18. A process for making surgical needles, comprising:
   a) providing needle blanks consisting essentially of martensitic precipitation hardening stainless steel,
   b) forming said needle blanks into surgical needles, then
   c) hardening said surgical needles by heating said surgical needles under vacuum at a temperature in the temperature range of from about 350° C. to about 550° C. for a period of time in the range of from about 15 minutes to about 20 hours, and then
   d) cooling said heated surgical needles in the absence of oxygen from said heating temperature to a temperature in the range of from about 150° C. to about ambient temperature.

19. The process of claim 18 wherein said step of forming said surgical needles comprises at least one step selected from the group consisting of sharpening a first end of said needle blank, tapering, bending, and drilling a hole in a second end of said needle blank.

20. The process of claim 18 further comprising the step:
   e) contacting said cooled needles with an inert gas prior to exposing said cooled needles to oxygen.

* * * * *